United States Patent [19] | [11] 4,081,327
Chibata et al. | [45] * Mar. 28, 1978

[54] PREPARATION OF D-FRUCTOSE

[75] Inventors: Ichiro Chibata, Suita; Tetsuya Tosa, Kyoto; Tadashi Sato, Takatsuki, all of Japan

[73] Assignee: Tanabe Seiyaku Co., Ltd., Osaka, Japan

[ * ] Notice: The portion of the term of this patent subsequent to Feb. 12, 1991, has been disclaimed.

[21] Appl. No.: 461,509

[22] Filed: Apr. 17, 1974

[30] Foreign Application Priority Data

Apr. 25, 1973 Japan ................................ 48-48714

[51] Int. Cl.$^2$ ....................... C12D 13/00; C12K 1/00; C07G 7/02

[52] U.S. Cl. .................................... 195/31 F; 195/54; 195/59; 195/63; 195/68; 195/DIG. 11

[58] Field of Search .................. 195/31 F, 64, 59, 63, 195/68, DIG. 11, 102, 31 R

[56] References Cited

U.S. PATENT DOCUMENTS

| | | | |
|---|---|---|---|
| 3,788,950 | 1/1974 | Hicks et al. | 195/63 X |
| 3,791,926 | 2/1974 | Chibata et al. | 195/59 X |
| 3,817,832 | 2/1974 | Lloyd et al. | 195/31 F |
| 3,843,442 | 10/1974 | Moskowitz | 195/31 F |

OTHER PUBLICATIONS

Strandberg et al., Free and Immobilized Glucose Isomerase from *Streptomyces Phaeochromogenes,* Applied Microbiology, vol. 21, No. 4, 1971 (pp. 588–593).

Franks, N. E., Catabolism of L–Arginine by Entrapped Cells of *Streptococcus Faecalis* ATCC 8043, Biochimica et Biophysica ACTA, vol. 252, 1971 (pp. 246–254).

*Primary Examiner*—David M. Naff
*Attorney, Agent, or Firm*—Bierman & Bierman

[57] ABSTRACT

An immobilized glucose isomerase-producing microorganism is reacted with D-glucose to produce D-fructose. Immobilization is carried out by polymerizing at least one acryloyl monomer in an aqueous suspension containing a glucose isomerase-producing microorganism. The acryloyl monomers employed include acryloylamide, N,N'-lower alkylene-bis-acryloylamide, bis(acryloylamidomethyl)ether and N,N'-di-acryloylethyleneurea.

14 Claims, No Drawings

PREPARATION OF D-FRUCTOSE

This invention relates to a novel process for preparing D-fructose. More particularly, it relates to the production of D-fructose by enzymatic reaction of an immobilized glucose isomerase-producing microorganism with D-glucose.

D-Fructose is useful as a sweeting agent. It is known in the art that glucose isomerase has the ability to convert D-glucose to D-fructose. Various methods are known for producing D-fructose from D-glucose by enzymatic reaction of glucose isomerase. For example, D-fructose can be prepared by cultivating a glucose isomerase-producing microorganism in a nutrient medium containing D-glucose. Alternatively, it can be prepared by extracting glucose isomerase from a microorganism, and reacting the enzyme with D-glucose. However, these methods are disadvantageous in the commercial production of D-fructose. D-Fructose produced according to these methods is contaminated with the enzyme, microbial cells, nutrient sources of the medium and/or protein. Accordingly, in order to recover D-fructose having high purity, additional steps for removing the enzyme and other contaminants from the product are required. Furthermore, when the enzymatic reaction is completed, the reaction solution is boiled and/or acidified to denature the enzyme or microorganism, and precipitates of the enzyme or microorganism are filtered off. Thus, glucose isomerase or the glucose isomerase-producing microorganism can be used only once and must be discarded thereafter.

One object of the present invention is to provide a novel immobilized microorganism which affords high activity of glucose isomerase for a long period of time. Another object of the invention is to provide an immobilized glucose isomerase-producing microorganism which obviates the necessity of discarding the microorganism and allows reuse thereof in a number of successive operations. Yet another object of the invention is to provide an improved method of preparing D-fructose from D-glucose by the use of a glucose isomerase-producing microorganism. Further objects of this invention will be apparent from the descriptions which follow.

According to the present invention, D-fructose can be prepared by polymerizing at least one acryloyl monomer in an aqueous suspension containing a glucose isomerase-producing microorganism to produce an immobilized glucose isomerase-producing microorganism, and subjecting the immobilized glucose isomerase-producing microorganism to enzymatic reaction with D-glucose.

Preferred examples of glucose isomerase-producing microorganisms which are employed in the present invention include *Streptomyces griseus* IFO (Institute of Fermentation, Osaka, Japan) 3430, *Streptomyces griseus* IFO 3356, *Streptomyces aureus* IFO 3175, *Streptomyces olivaceus* IFO 3409 and *Bacillus coagulans* IFO 12714. All of these microorganisms are publicly available from the above-mentioned depository. In this connection, however, it should be noted that the present invention is not limited to the use of these specific microorganisms, but includes within its scope the use of all glucose isomerase-producing microorganisms. Suitable amounts of glucose isomerase-producing microorganisms employed in the present invention are in the range of 0.25 to 2.5 g, especially 0.5 to 2.0 g, per g of the acryloyl monomers used. The polymerization reaction of the present invention serves to tightly entrap the microorganisms into the lattice of the polymer thereby affording high enzymatic activity for a long period of time.

The polymerization reaction of the present invention can be carried out in the presence of a polymerization initiator and a polymerization accelerator. Potassium persulfate, ammonium persulfate, vitamin $B_2$ and methylene blue are suitable as polymerization initiators. On the other hand, $\beta$-(dimethylamino)-propionitrile and N,N,N',N'-tetramethylethylenediamine are employed as the polymerization accelerator. Suitable amount of the polymerization initiator which is added to the aqueous suspension of the glucose isomerase-producing microorganism is 1 to 100 mg, especially 5 to 50 mg, per g of the acryloyl monomer or monomers. Suitable amount of the polymerization accelerator to be added is 1 to 100 mg, especially 10 to 50 mg, per g of the acryloyl monomer or monomers. It is preferred to carry out the reaction at 0° to 50° C, especially at 20° to 40° C. The reaction may be completed within 10 to 60 minutes. The acryloyl monomers which are suitable for use in the present invention include acryloylamide, N,N'-lower alkylene-bis-acryloylamide, bis(acryloylamidomethyl) ether and N,N'-di-acryloyl-ethyleneurea(=N,N'-diacryloylimidazolidine-2-one). For the purpose of the present invention, it is suitable to entrap the glucose isomerase-producing microorganism with a polymer obtained from one or two monomers mentioned above, particularly with a copolymer of acryloylamide and an acryloyl monomer selected from the group consisting of N,N'-lower alkylene-bis-acryloylamide, bis(acryloylamidomethyl) ether and N,N'-di-acryloylethyleneurea, or with a homopolymer of N,N'-lower alkylene-bis-acryloylamide, bis(acryloylamidomethyl)ether or N,N'-di-acryloyl-ethyleneurea. N,N'-methylene-bis-acryloylamide and N,N'-propylene-bis-acryloylamide are preferably employed as the N,N'-lower alkylene-bis-acryloylamide. Suitable amount of N,N'-lower alkylene-bis-acryloylamide, bis (acryloylamidomethyl)ether or N,N'-di-acryloylethyleneurea which is used to copolymerize with acryloylamide is 5 to 160 mg, especially 25 to 80 mg, per g of acryloylamide. After the polymerization reaction is completed as above, the resultant immobilized glucose isomerase-producing microorganism is granulated by passing it through a sieve to form granules of 1 to 10 mm, especially 3 to 4 mm in diameter.

D-Fructose can be prepared from D-glucose by enzymatic reaction of the immobilized glucose isomerase-producing microorganism. The enzymatic reaction is carried out at 20° to 80° C, especially at 40° to 70° C. It is preferred to carry out the reaction at a pH of 6 to 9, especially at pH 7 to 8.5. In carrying out the enzymatic reaction of the invention, the enzymatic activity can be stabilized effectively by adding magnesium and cobaltous ions to the reaction solution. Suitable amount of magnesium ion added to the reaction solution is 1 to 20 millimoles, especially 3 to 10 millimoles, per liter of the reaction solution. Suitable amount of cobaltous ion added to the reaction solution is 0.1 to 10 millimoles, especially 0.5 to 5 millimoles, per liter of the reaction solution. The concentration of a substrate employed is not critical in the present invention. For example, D-glucose is dissolved in water at any concentration. The aforementioned immobilized microorganism is suspended in the solution of D-glucose, and the suspension is stirred. After the reaction is completed, the mixture is filtered or centrifuged to recover the immobilized microorganism for subsequent use. An aqueous solution containing D-fructose is obtained as the filtrate or the supernatant solution. D-Fructose is recovered by known methods such as, for example, by the steps of adding boric acid or a borate (e.g., sodium tetraborate) to the filtrate or the supernatant solution, and treating the mixture with a strong basic anion-exchange resin. Optimum reaction conditions for conversion of D-glucose to D-fructose can be readily determined by adjusting the reaction time.

Alternatively, the enzymatic reaction of the present invention can be performed by a column method. The column method enables the reaction to be carried out in a successive manner. For example, the immobilized microorganism is charged into a column, and an aqueous solution of D-glucose is passed through the column at a suitable flow rate. An aqueous solution containing D-fructose is obtained as the effluent. D-Fructose is recovered from the effluent by the same method as applied to the above-mentioned filtrate or the supernatant solution. In carrying out the enzymatic reaction, the conversion rate of D-glucose to D-fructose mainly depends upon the enzymatic potency of the immobilized microorganism, the temperature and/or the reaction time. In the case of the column method, however, the optimum reaction condition for conversion of D-glucose to D-fractose can be readily obtained by adjusting the flow rate of the substrate solution.

In any case, the immobilized microorganism of the present invention retains a high level of enzymatic activity during the reaction, especially in the presence of magnesium and cobaltous ions. Moreover, due to the sufficient durability of the enzymatic activity thereof, the immobilized microorganism of the invention can be used repeatedly for the enzymatic reaction.

Practical and presently-preferred embodiments of the present invention are shown in the following Examples. In this specification, the terminology "lower alkylene" should be interpreted as referring to alkylene groups having one a four carbon atoms. In the following Examples, the potency of a microorganism or immobilized microorganism which afforded 1 mg of D-fructose on the reaction of the microorganism or immobilized microorganism with D-glucose at pH 8.0 to 60° C for an hour was taken as 1 unit. The identification of D-fructose in a solution was performed by paper chromatography in which a mixture of n-butanol, acetic acid and water (4 : 1 : 1) was used as the developing solvent. The amount of D-fructose in a solution was assayed in accordance with the method of M. C. Cadmus et al[-Analytical Biochemistry, Volume 26, Pages 484 - 487(1968)]. That is, 0.4 ml of a D-fructose solution were added to a mixture of 0.1 ml of 20% L-cysteine hydrochloride hydrate and 5 ml of 75%(v/v) sulfuric acid. The mixture is stirred and then alowed to stand for an hour. The amount of D-fructose in the mixture was assayed colorimetrically.

EXAMPLE 1

(1) An aqueous nutrient medium (pH 7.0) containing the following ingredients is prepared:

| | | |
|---|---|---|
| Peptone | 1 | (w/v %) |
| Yeast extract | 0.25 | |
| Meat extract | 0.5 | |
| D-glucose | 0.3 | |
| D-xylose | 0.7 | |

-continued

| | |
|---|---|
| Magnesium sulfate 7 hydrate | 0.05 |
| Cobaltous chloride 6 hydrate | 0.024 |
| sodium chloride | 0.5 |

*Streptomyces griseus* IFO 3430 is inoculated into 200 ml of the medium. The medium is cultivated at 30° C for 72 hours under shaking. The medium is then centrifuged. The microbial cells thus collected show the glucose isomerase activity of 30 units/g. 17 g of the microbial cells are suspended in 68 ml of a physiological saline solution. 12.75 g of acryloylamide, 680 mg of N,N'-methylene-bis-acryloylamide, 7.5 ml of 5 % β-(dimethylamino)-propionitrile and 7.5 ml of 2.5 % potassium persulfate are added to the suspension. Then, the suspension is allowed to stand at 37° C for 30 minutes. After the reaction is completed, the stiff gel thus obtained is granulated by passing it through a sieve to form granules of 3 mm in diameter. Then, the granules are washed with 1700 ml of a physiological saline solution. 170 ml of an immobilized preparation of *Streptomyces griseus* IFO 3430 are obtained. Glucose isomerase activity: 25 units/ml.

(2) 170 ml of the immobilized preparation of *Streptomyces griseus* IFO 3430 are charged into a 4 cm × 13.5 cm column. 200 ml of an aqueous 40% D-glucose solution (pH 8.0) containing 5 mM-concentration of magnesium ion and 1 mM-concentration of cobaltous ion are passed through the column at 60° C at the flow rate of 60 ml/hr. 200 ml of an aqueous 0.04 M sodium tetraborate solution are added to 200 ml of the effluent. Then, the mixture is passed through the column of an ion-exchange resin [manufactured by Dow Chemical Co., under the trade name "Dowex 1 × 2 ($H^+$ type)"]which was previously washed with an aqueous 0.02 M sodium tetraborate solution. The effluent is then passed through the column of an ion-exchange resin [manufactured by Dow Chemical Co., under the trade name "Dowex 50 × 8 ($H^+$type)"]. The effluent is concentrated. 13.9 g of a syrup of D-fructose are obtained. The D-fructose content in the syrup is 90%.

EXAMPLE 2

(1) *Streptomyces aureus*IFO 3175 is inoculated into 200 ml of an aqueous nutrient medium (pH 7.0) having the same composition as described in Example 1. The medium is cultivated at 30° C for 72 hours under shaking. Then, the medium is centrifuged. The microbial cells thus collected show the glucose isomerase activity of 15 units/g. 12 g of the microbial cells are suspended in 48 ml of a physiological saline solution. 9 g of acryloylamide, 480 mg of N,N'-methylene-bis-acryloylamide, 6 ml of 5% β-(dimethylamino)-propionitrile and 6 ml of 2.5% potassium persulfate are added to the suspension. Then, the suspension is allowed to stand at 37° C for 30 minutes. After the reaction is completed, the stiff gel thus obtained is granulated by passing it through a sieve to form granules of 3 mm in diameter. Then, the granules are washed with 1200 ml of a physiological saline solution. 120 ml of an immobilized preparation of *Streptomyces aureus* IFO 3175 are obtained. Glucose isomerase activity: 10 units/ml.

(2) 120 ml of the immobilized preparation of *Streptomyces aureus* IFO 3175 are suspended in 400 ml of an aqueous 40% D-glucose solution (pH 8.0) containing 5 mM-concentration of magnesium ion and 1 mM-concentration of cobaltous ion. The suspension is stirred at 60° C for a certain period of time. The D-fructose content in the suspension is assayed, and the percentage conversion of D-glucose to D-fructose is calculated therefrom. The results are shown in Table 1.

Table 1

| Reaction time (hr.) | Conversion to D-fructose (%) |
|---|---|
| 3 | 11 |
| 7 | 20 |
| 16 | 41 |
| 20 | 47 |
| 48 | 46 |

After stirring 48 hours, the suspension is filtered to remove the immobilized preparation. The filtrate is treated in the same manner as described in Example 1. 30.1 g of a syrup of D-fructose are obtained. The D-fructose content in the syrup is 87%.

EXAMPLE 3

(1) *Streptomyces olibaceus* IFO 3409 is inoculated into 100 ml of an aqueous nutrient medium (pH 7.0) having the same composition as described in Example 1. The medium is cultivated at 30° C for 72 hours. Then, the medium is centrifuged. The microbial cells thus collected show the glucose isomerase activity of 9 units/g. 5 g of the microbial cells are suspended in 20 ml of a physiological saline solution. 3.75 g of acryloylamide, 200 mg of bis(acryloylamidomethyl)ether, 2.5 ml of 5% β-(dimethylamino)-propionitrile and 2.5 ml of 1% ammonium persulfate are added to the suspension. Then, the suspension is allowed to stand at 37° C for 30 minutes. After the reaction is completed, the stiff gel thus obtained is granulated by passing it through a sieve to form granules of 3 mm in diameter. Then, the granules are washed with 500 ml of a physiological saline solution. 50 ml of an immobilized preparation of *Streptomyces olibaceus* IFO 3409 are obtained. Glucose isomerase activity: 6 units/ml.

(2) 50 ml of the immobilized preparation of *Streptomyces olibaceus* IFO 3409 are charged into a 2 cm × 16 cm column. An aqueous 40% D-glucose solution (pH 8.0) containing 5 mM-concentration of magnesium ion and 1 mM-concentration cobaltous ion is passed through the column at a flow rate, as shown in Tabel 2. The D-fractose content in the effluent is assayed, and the percentage conversion of D-glucose to D-fructose is calculated therefrom. The results are shown in Table 2.

Table 2

| Operation time (hr) | Conversion (%) to D-fructose, Flow rate 12.5 ml/hr | Conversion (%) to D-fructose, Flow rate 6.5 ml/hr |
|---|---|---|
| 5 | 28.2 | 40.2 |
| 24 | 25.2 | 39.4 |
| 48 | 26.2 | 40.0 |
| 72 | 26.3 | 40.3 |
| 96 | 25.8 | 39.9 |
| 112 | 26.2 | 40.0 |

EXAMPLE 4

(1) An aqueous nutrient medium (pH 7.0) containing the following ingredients is prepared:

| | | |
|---|---|---|
| Yeast extract | 0.3 | (w/v %) |
| D-glucose | 2 | |
| Ammonium chloride | 0.3 | |

-continued

| | |
|---|---|
| Dipotassium phosphate | 0.1 |
| Magnesium sulfate 7 hydrate | 0.05 |
| Manganous sulfate 4 hydrate | 0.005 |
| Calcium carbonate | 0.2 |

*Bacillus coagulans* IFO 12714 is inoculated into one liter of the medium. The medium is cultivated at 37° C for 24 hours. Then, one liter of an aqueous solution containing 3 w/v % of peptone and 2 w/v % of D-xylose is added to the medium. The medium is allowed to stand at 37° C for 6 hours. The medium is centrifuged. The microbial cells thus collected show the glucose isomerase activity of 7 units/g. 12 g of the microbial cells are suspended in 68 ml of physiological saline solution. 9 g of acryloylamide, 480 mg of N,N'-methylene-bis-acryloylamide, 6 ml of 5% β-(dimethylamino)-propionitrile and 6 ml of 2.5% potassium persulfate are added to the suspension. The suspension is allowed to stand at 37° C for 30 minutes. After the reaction is completed, the stiff gel thus obtained is granulated by passing it through a sieve to form granules of 3 mm in diameter. Then, the granules are washed with 1200 ml of a physiological saline solution. 120 ml of an immobilized preparation of *Bacillus coagulans* IFO 12714 are obtained. Glucose isomerase activity: 5 units/ml.

(2) 120 ml of the immobilized preparation of *Bacillus coagulans* IFO 12714 are suspended in 400 ml of an aqueous 40% D-glucose solution (pH 8.0) containing 5 mM-concentration of magnesium ion and 1 mM-concentration of cobaltous ion. The suspension is stirred at 45° C for 96 hours, and then filtered to remove the immobilized preparation. The filtrate is treated in the same manner as described in Example 1. 22.6 g of a syrup of D-fructose are obtained. The D-fructose content in the syrup is 81%.

EXAMPLE 5

(1) 12 g of the microbial cells of *Streptomyces griseus* IFO 3430 are suspended in 48 ml of a physiological saline solution. 9 g of acryloylamide, 480 mg of N,N'-diacryloylethylene urea, 6 ml of 5% β-(dimethylamino)-propionitrile and 6 ml of 2.5 % ammonium persulfate are added to the suspension. Then, the suspension is allowed to stand at 37° C for 30 minutes. The obtained stiff gel is granulated by passing it through a sieve to form granules of 3 mm in diameter. Then, the granules are washed with 1200 ml of a physiological saline solution. 120 ml of an immobilized preparation of *Streptomyces griseus* IFO 3430 are obtained. Glucose isomerase activity: 15 units/ml.

(2) 120 ml of the immobilized preparation of *Streptomyces griseus* IFO 3430 are suspended in 400 ml of an aqueous 40% D-glucose solution (pH 8.0) containing 5 mM-concentration of magnesium ion and 1 mM-concentration of cobaltous ion. The suspension is stirred at 60° C for 48 hours, and then filtered to remove the immobilized preparation. The filtrate is treated in the same manner as described in Example 1. 27.8 g of a syrup of D-fructose are obtained. The D-fructose content in the syrup is 90%.

EXAMPLE 6

(1) 24 g of the microbial cells of *Streptomyces griseus* IFO 3430 are suspended into 240 ml of a physiological saline solution. 600 mg of bis(acryloylamido methyl)ether, 18 ml of 0.112% N,N,N', N'-tetramethylethylenediamine and 2 ml of 2.5% ammonium persulfate are added to the suspension. Then, the suspension is allowed to stand at 37° C for 60 minutes. The obtained stiff gel is granulated by passing it through a sieve to form granules of 3 mm in diameter. Then, the granules are washed with 4200 ml of a physiological saline solution. 420 ml of the immobilized preparation of *Streptomyces griseus* IFO 3430 are obtained. Glucose isomerase activity: 4 units/ml.

(2) 420 ml of the immobilized preparation of *Streptomyces griseus* IFO 3430 are suspended in 400 ml of an aqueous 40% D-glucose solution (pH 8.0) containing 5 mM-concentration of magnesium ion and 1 mM-concentration of cobaltous ion. The suspension is stirred at 60° C for 72 hours, and then filtered to remove the immobilized preparation. The filtrate is treated in the same manner as described in Example 1. 27.8 g of a syrup of D-fructose are obtained. The D-fructose content in the syrup is 90%.

EXAMPLE 7

(1) 24 g of the microbial cells of *Streptomyces griseus* IFO 3430 are suspended into 240 ml of a physiological saline solution. 600 mg of N,N'-di-acryloyl-ethylene urea, 18 ml of 0.112% N,N,N',N'-tetramethyl-ethylenediamine and 2 ml of 2.5% potassium persulfate are added to the suspension. Then, the suspension is allowed to stand at 30° C for 30 minutes. The obtained stiff gel is granulated by passing it through a sieve to form granules of 3 mm in diameter. Then, the granules are washed with 4200 ml of a physiological saline solution. 420 ml of the immobilized preparation of *Streptomyces griseus* IFO 3430 are obtained. Glucose isomerase activity: 3 units/ml.

(2) 420 ml of the immobilized preparation of *Streptomyces griseus* IFO 3430 are suspended in 400 ml of an aqueous 40% D-glucose solution (pH 8.0) containing 5 mM-concentration of magnesium ion and 1 mM-concentration of cobaltous ion. The suspension is stirred at 60° C for 72 hours, and then filtered to remove the immobilized preparation. The filtrate is treated in the same manner as described in Example 1. 27.8 g of syrup of D-fructose are obtained. The D-fructose content in the syrup is 90%.

EXAMPLE 8

(1) 24 g of the microbial cells of *Streptomyces griseus* IFO 3430 are suspended into 240 ml of a physiological saline solution. 600 mg of N,N'-methylene-bis-acryloylamide, 18 ml of 0.112% N,N,N',N'-tetramethyl-ethylenediamine and 2 ml of 2.5% potassium persulfate are added to the suspension. Then, the suspension is allowed to stand at 37° C for 60 minutes. The obtained stiff gel is granulated by passing it through a sieve to form granules of 3 mm in diameter. Then, the granules are washed with 4200 ml of a physiological saline solution. 420 ml of the immobilized preparation of *Streptomyces griseus* IFO 3430 are obtained. Glucose isomerase activity: 5 units/ml.

(2) 420 ml of the immobilized preparation of *Streptomyces griseus* IFO 3430 are suspended in 400 ml of an aqueous 40% D-glucose solution (pH 8.0) containing 5 mM-concentration of magnesium ion and 1 mM-concentration of cobaltous ion. The suspension is stirred at 60° C for 72 hours, and then filtered to remove the immobilized preparation. The filtrate is treated in the same manner as described in Example 1. 27.8 g of a syrup of D-fructose are obtained. The D-fructose content in the syrup is 90%.

EXAMPLE 9

60 ml of the immobilized preparation of *Streptomyces griseus* IFO 3430 which prepared in the same manner as described in Example 1 are suspended in 200 ml of an aqueous 40% D-glucose solution (pH 8.0) containing 5 mM-concentration of magnesium ion and 1 mM-concentration of cobaltous ion or in 200 ml of an aqueous 40% D-glucose solution (pH 8.0), respectively. The suspensions are stirred at 60° C for a certain period of time. The D-fructose content in the suspension is assayed, and the percentage conversion of D-glucose to D-fructose is calculated therefrom. The results are shown in Table 3.

Table 3

| Reaction time (hr) | Conversion to D-fructose (%) | |
|---|---|---|
| | Addition of metal ion | No addition |
| 3 | 22 | 4 |
| 5 | 31 | 6 |
| 16 | 46 | 14 |
| 24 | 45 | 22 |
| 48 | 47 | 31 |
| 72 | 46 | 39 |

What we claim is:

1. An immobilized glucose isomerase-producing microorganism comprising a glucose isomerase-producing microorganism tightly entrapped in the lattice of a semi-permeable acryloyl polymer selected from the group consisting of homopolymer of N,N'-lower alkylene-bis-acryloylamide, bis(acryloylamidomethyl) ether or N,N'-di-acryloyl-ethyleneurea, copolymer of acryloylamide and N,N'-lower alkylene-bis-acryloylamide, copolymer of acryloylamide and bis(acryloyl amidomethyl)ether and copolymer of acryloylamide and N,N'-di-acryloyl-ethyleneurea.

2. The immobilized glucose isomerase-producing microorganism as claimed in claim 1, wherein 0.25 to 2.5 g, per g of the acryloyl polymer, of the glucose isomerase-producing microorganism is entrapped.

3. The immobilized glucose isomerase-producing microorganism as claimed in claim 1, wherein said semi-permeable acryloyl polymer is granules of 1 to 10 mm in diameter.

4. The immobilized glucose isomerase-producing microorganism as claimed in claim 1, wherein 0.25 to 2.5 g, per g of the acryloyl polymer, of the glucose isomerase-producing microorganism is entrapped in a copolymer of acryloylamide and 5 to 160 mg, per g of acryloylamide, of N,N'-lower alkylene-bis-acryloylamide, bis(acryloylamidomethyl)ether or N,N'-diacryloyl-ethyleneurea.

5. The immobilized glucose isomerase-producing microorganism according to claim 1 wherein said glucose isomerase-producing microorganism is *Streptomyces griseus* IFO 3430, *Streptomyces griseus* IFO 3356, *Streptomyces aureus* IFO 3175, *Streptomyces olivaceus* IFO 3409, or *Bacillus coagulans* IFO 12714.

6. A process for preparing D-fructose which comprises the steps of polymerizing N,N'-lower alkylene-bis-acryloyl-amide, bis(acryloylamidomethyl)ether or N,N'-di-acryloyl-ethyleneurea, or copolymerizing acryloylamide with N,N'-lower alkylene-bis-acryloylamide, bis(acryloylamidomethyl)ether or N,N'-di-acryloyl-ethyleneurea, in an aqueous suspension of a glucose isomerase-producing microorganism in the presence of a polymerization initiator and a polymerization accelerator to produce an immobilized glucose isomerase-producing microorganism, and subjecting the immobilized glucose isomerase-producing microorganism to enzymatic reaction with D-glucose in the presence of magnesium and cobaltous ions.

7. The process according to claim 6, wherein the polymerization is carried out at 0° to 50° C, and the enzymatic reaction is carried out at 20° to 80° C at a pH of 6 to 9.

8. The process according to claim 6, wherein the polymerization is carried out 20° to 40° C, and the enzymatic reaction is carried out at 50° to 70° C.

9. The process according to claim 6, wherein the polymerization initiator is selected from the group consisting of potassium persulfate, ammonium persulfate, vitamin $B_2$ and methylene blue, and the polymerization accelerator is selected from the group consisting of $\beta$-(dimethylamino)-propionitrile and N,N,N', N'-tetramethyl-ethylenediamine.

10. The process according to claim 6, wherein the glucose isomerase-producing microorganism is selected from the group consisting of *Streptomyces griseus* IFO 3430, *Streptomyces griseus* IFO 3356, *Streptomyces aureus* IFO 3175, *Streptomyces olivaceus* IFO 3409 and *Bacillus coagulans* IFO 12714.

11. A process for preparing D-fructose which comprises the steps of polymerizing N,N'-lower alkylene-bis-acryloylamide, bis(acryloylamidomethyl)ether or N,N'-di-acryloyl-ethyleneurea in an aqueous suspension containing 0.25 to 2.5 g, per g of the acryloyl monomer, of a glucose isomerase-producing microorgansim in the presence of 1 to 100 mg, per g of the acryloyl monomer, of a polymerization initiator and 1 to 100 mg, per g of the acryloyl monomer, of a polymerization accelerator at 0° to 50° C, forming granules of the immobilized glucose isomerase-producing microorganism, and then subjecting said granules of the immobilized microorganism to enzymatic reaction with D-glucose at 20° to 80° C at a pH 6 to 9 in the presence of 1 to 20 millimoles of magnesium ion and 0.1 to 10 millimoles of cobaltous ion per liter of the reaction solution.

12. The process according to claim 11, wherein the polymerization initiator is selected from the group consisting of potassium persulfate, ammonium persulfate, vitamin $B_2$ and methylene blue, and the polymerization accelerator is selected from the group consisting of $\beta$-(dimethylamino)-propionitrile and N,N,N'N'-tetramethyl-ethylenediamine.

13. A process for preparing D-fructose which comprises the steps of copolymerizing acryloylamide with 5 to 160 mg, per g of acryloylamide, of N,N'-lower alkylene-bis-acryloylamide, bis(acryloylamidomethyl)ether or N,N'-di-acryloylethyleneurea in an aqueous suspension containing 0.25 to 2.5 g, per g of the acryloyl monomers, of a glucose isomerase-producing microorganism in the presence of 1 to 100 mg, per g of the acryloyl monomers, of a polymerization initiator and 1 to 100 mg, per g of the acryloyl monomers, of a polymerization accelerator at 0° to 50° C, forming granules of the immobilized glucose isomerase-producing microorganism, and then subjecting said granules of the immobilized microorganism to enzymatic reaction with D-glucose at 20° to 80° C at a pH 6 to 9 in the presence of 1 to 20 millimoles of magnesium ion and 0.1 to 10 millimoles of cobaltous ion per liter of the reaction solution.

14. The process according to claim 13, wherein the polymerization initiator is selected from the group consisting of potassium persulfate, ammonium persulfate, vitamin $B_2$ and methylene blue, and the polymerization accelerator is selected from the group consisting of $\beta$-(dimethylamino)-propionitrile and N,N,N',N'-tetramethyl-ethylenediamine.

* * * * *